United States Patent
Reisfeld et al.

(10) Patent No.: US 11,826,149 B2
(45) Date of Patent: Nov. 28, 2023

(54) ELECTROCARDIOGRAM GAIN ADJUSTMENT

(71) Applicant: Medtronic, Inc., Minneapolis, MN (US)

(72) Inventors: Erin N. Reisfeld, Minneapolis, MN (US); Joseph C. Green, Brooklyn Park, MN (US); Ryan D. Wyszynski, Oak Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 268 days.

(21) Appl. No.: 17/086,950

(22) Filed: Nov. 2, 2020

(65) Prior Publication Data
US 2022/0133168 A1 May 5, 2022

(51) Int. Cl.
| | | |
|---|---|---|
| *A61B 5/349* | (2021.01) | |
| *A61B 5/339* | (2021.01) | |
| *A61B 5/352* | (2021.01) | |
| *A61B 5/287* | (2021.01) | |
| *A61B 5/00* | (2006.01) | |

(52) U.S. Cl.
CPC ............ *A61B 5/349* (2021.01); *A61B 5/0006* (2013.01); *A61B 5/0031* (2013.01); *A61B 5/287* (2021.01); *A61B 5/339* (2021.01); *A61B 5/352* (2021.01); *A61B 5/686* (2013.01); *A61B 5/4836* (2013.01)

(58) Field of Classification Search
None
See application file for complete search history.

(56) References Cited

U.S. PATENT DOCUMENTS

| | | | |
|---|---|---|---|
| 3,809,071 A * | 5/1974 | Davolos | A61B 5/0006 600/515 |
| 6,745,076 B2 | 6/2004 | Wohlgemuth et al. | |
| 7,945,314 B1 | 5/2011 | Snell et al. | |
| 8,321,001 B2 | 11/2012 | Doerr | |
| 9,619,660 B1 | 4/2017 | Felix et al. | |
| 9,936,890 B2 | 4/2018 | Sarkar et al. | |
| 10,512,784 B2 | 12/2019 | Hahn et al. | |
| 10,799,137 B2 * | 10/2020 | Bardy | A61B 5/316 |
| 2003/0144572 A1 * | 7/2003 | Oschman | A61M 60/196 607/117 |
| 2005/0027321 A1 * | 2/2005 | Ferek-Petric | A61B 5/349 607/9 |
| 2005/0288726 A1 * | 12/2005 | Gollasch | A61B 5/0537 607/17 |

(Continued)

FOREIGN PATENT DOCUMENTS

| | | | | |
|---|---|---|---|---|
| EP | 3620107 A1 * | 3/2020 | ......... | A61B 5/04012 |
| EP | 3620107 A1 | 3/2020 | | |

OTHER PUBLICATIONS

International Search Report and Written Opinion of International Application No. PCT/US2021/051203, dated Jan. 19, 2022, 8 pp.

(Continued)

*Primary Examiner* — Matthew Kremer
*Assistant Examiner* — Matthew Eric Ogles
(74) *Attorney, Agent, or Firm* — Shumaker & Sieffert, P.A.

(57) ABSTRACT

A method comprises identifying P-waves within a cardiac signal stored by a medical device for a cardiac episode detected by the medical device, and calculating a gain factor for display of the cardiac signal based on the identified P-waves.

19 Claims, 8 Drawing Sheets

(56) References Cited

U.S. PATENT DOCUMENTS

| | | | |
|---|---|---|---|
| 2011/0106200 A1* | 5/2011 | Ziegler | A61B 5/7275 |
| | | | 607/18 |
| 2011/0137190 A1* | 6/2011 | Katz | A61B 5/349 |
| | | | 600/509 |
| 2012/0296388 A1* | 11/2012 | Zhang | A61B 7/04 |
| | | | 607/18 |
| 2014/0303470 A1* | 10/2014 | Tsukada | D06M 13/148 |
| | | | 428/394 |
| 2015/0282734 A1* | 10/2015 | Schweikert | A61B 5/318 |
| | | | 600/424 |
| 2016/0213273 A1 | 7/2016 | Cao et al. | |
| 2016/0235992 A1* | 8/2016 | Sarkar | A61B 5/316 |
| 2019/0275339 A1 | 9/2019 | Ghosh et al. | |
| 2019/0336031 A1 | 11/2019 | Malhotra et al. | |
| 2019/0357794 A1* | 11/2019 | Bardy | A61B 5/7203 |
| 2020/0085333 A1* | 3/2020 | Freed | A61B 5/361 |

OTHER PUBLICATIONS

Karimipour et al., "Real-Time Electrocardiogram P-QRS-T Detection—Delineation Algorithm Based on Quality-Supported Analysis of Characteristic Templates," Computers in Biology and Medicine, No. 52, Jul. 2014, pp. 153-165.

* cited by examiner

ELECTROCARDIOGRAM GAIN ADJUSTMENT

TECHNICAL FIELD

This disclosure generally relates to electrocardiograms or other cardiac signals, and more specifically, adjustment of displays of such signals.

BACKGROUND

An electrocardiograms (ECG) represents the electric signals of a patient's heart. ECGs collected by a medical device may be stored and/or displayed in a waveform format. In an ECG display, the P-wave represents depolarization of the atria, the Q, R, and S-waves represents the depolarization of the ventricles, and the T-wave represents repolarization of the ventricles. ECGs may be used to detect or observe a range of heart conditions including arrhythmias.

SUMMARY

In general, this disclosure is directed to the adjustment of gain factors for displaying ECGs or other cardiac signals. More particularly, the disclosure is directed to techniques for adjusting the gain factor for displaying a cardiac signal that include detecting P-waves in ECGs and calculating gain factors for the display of the cardiac signal based on the identified P-waves.

In some examples, a medical device detects cardiac episodes based on its analysis of cardiac signals sensed via its electrodes, and stores a portion of the cardiac signal, e.g., an ECG, as part of the record for that episode. Another device may display the stored ECG for the episode for review by a clinician. However, such devices typically set the gain factor for displaying the ECG based on the R-waves in the stored ECG. In some examples, the techniques of this disclosure may involve determining that a detected cardiac episode is an atrial arrhythmia or other episode in which P-waves would be of interest, and calculating, e.g., automatically, the gain factor based on the identified P-waves of the cardiac episode when the episode is an atrial arrhythmia or other episode in which P-waves would be of interest. For other episodes, e.g., ventricular arrhythmias, the techniques may include calculating the gain factor for displaying the episode based on other information, such as one or more features of R-waves within the episode. In some examples, different gain factors are calculated and applied to different portions or windows of the same episode, e.g., a first gain factor calculated based on P-waves for displaying one or more portions or windows of the episode that include P-waves, and a second gain factor calculated based on R-waves for displaying one or more portions or windows of the episode that include R-waves.

The techniques of this disclosure may also involve determining a zoom factor, e.g., to allow a clinician to selectively zoom in on a portion of ECG, based on the gain factor that was determined based on one or more features of the P-waves. The P-waves may be identified by averaging segments of the cardiac signal of the cardiac episode that are associated with R-waves meeting a certain selection criterion, and identifying P-waves based on a derivative of the average of the segments. The gain factor may be calculated by determining the amplitude of the P-waves and determining an average P-wave amplitude.

In some examples, a method comprises identifying P-waves within a cardiac signal stored by a medical device for a cardiac episode detected by the medical device, and calculating a gain factor for display of the cardiac signal based on the identified P-waves.

In some examples, a medical device system comprises processing circuitry that is configured to identify P-waves within a cardiac signal stored by a medical device for a cardiac episode detected by the medical device. The processing circuitry may be further configured to calculate a gain factor for display of the cardiac signal based on the identified P-waves.

In some examples, a non-transitory computer-readable storage system comprises instructions that, when executed by the processing circuitry of a medical device system, cause the processing circuitry to identify P-waves within a cardiac signal stored by a medical device for a cardiac episode detected by the medical device, and calculate a gain factor for display of the cardiac signal based on the identified P-waves.

The techniques of this disclosure may provide one or more advantages. For example, the techniques of this disclosure may simplify the observation of P-waves in the ECG display, e.g., in the case of episodes for which identification and analysis of P-waves are of interest. Because gain settings are typically based on the R-waves, clinicians may need to manually zoom in to observe the lower-amplitude P-waves, or may not be able to zoom in given the gain/zoom is configured for observation of the R-waves. The techniques of this disclosure simplify the process of analyzing P-waves in an ECG for an atrial arrhythmia episode or other episode in which such analysis will be of interest.

The summary is intended to provide an overview of the subject matter described in this disclosure. It is not intended to provide an exclusive or exhaustive explanation of the systems, device, and methods described in detail within the accompanying drawings and description below. The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

Like reference characters denote like elements throughout the description and figures.

DETAILED DESCRIPTION

A variety of types of medical devices sense and/or evaluate cardiac signals of a patient. Some medical devices that sense cardiac signals are non-invasive, e.g., using a plurality of electrodes placed in contact with external portions of a patient, such as at various locations on the skin of the patient. The electrodes used to monitor cardiac signals in these non-invasive processes may be attached to the patient using an adhesive, strap, belt, or vest, as examples, and electrically coupled to a monitoring device, such as an electrocardiograph. The electrodes are configured to sense electrical signals associated with the electrical activity of the heart, and to provide these sensed electrical signals to a medical device and/or computing device for further processing and/or display of the electrical signals. Such devices and methods may be utilized on a temporary basis, for example to monitor a patient during a clinical visit, such as during a doctor's appointment, or for example for a predetermined period of time, for example for one day (twenty-four hours), or for a period of several days.

Other external devices that may be used to non-invasively sense and monitor cardiac signals include wearable devices with electrodes configured to contact the skin of the patient, such as patches, watches, or necklaces. Such external devices may facilitate relatively longer-term monitoring of patients during normal daily activities and may periodically transmit collected data to a network service.

Implantable medical devices (IMDs) may also be used to sense and monitor cardiac signals. The electrodes used by IMDs to sense cardiac signals are typically integrated with a housing of the IMDs and/or coupled to the IMD via one or more elongated leads. Example IMDs that monitor cardiac signals include pacemakers and implantable cardioverter-defibrillators. Some IMDs that do not provide therapy, e.g., implantable patient monitors, sense cardiac signals. One example of such an IMD may be inserted subcutaneously. Such IMDs may facilitate relatively longer-term monitoring of patients during normal daily activities and may periodically transmit collected data to a network service.

Some wearable and implantable medical devices transmit ECGs and cardiac signals to a computing device which may display the cardiac signals to a user. For example, the medical devices may detect an episode based on its analysis of the cardiac signals sensed via electrodes and, in some cases, signals sensed via other physiological sensors, and store a segment or sample of the cardiac signals as part of a record of the episode. Example episodes include arrhythmias, falls, syncope, ectopic beats, or periods of exercise. Computing devices may be local to the patient or remote and in communication with the medical device via a network, and may include smartphones, medical device programmers, desktop computers, workstations, or servers.

Each cardiac cycle in a cardiac signal, e.g., an ECG signal, may contain several distinct components. The P-wave is the first recorded wave and represents the depolarization of the atria. The P-wave is followed by the Q-wave, R-wave, and the S-waves, which represent the depolarization of the ventricles. The T-waves follows the S-wave and represents the repolarization of the ventricles. The amplitude of the R-wave is generally significantly higher than the amplitude of the P-wave. The visibility and size of each component on a display is dependent on the gain factor applied to the signal recorded by the medical device for display.

A gain factor converts cardiac signal voltage to physical size values for an ECG display. The standard gain factor for an ECG display is 10 mm/mV. The gain factor may be increased or decreased and will affect the size of the ECG signals on the ECG display (e.g., height and/or depth of the waves of the ECG signal). Conventionally, the standard gain factor is automatically calculated using the average amplitude of R-waves in the cardiac signal.

In some instances, such as when the cardiac episode is an atrial arrhythmia episode, the user may want to adjust the gain factor to improve the visibility of particular components of the ECG display (e.g., P-waves). The user would need to use a zoom function manually adjust from the standard gain factor to improve the visibility of particular components of the ECG display. For example, if the standard gain factor is automatically calculated using the average amplitude of R-waves in the ECG, then the clinician must manually zoom to increase the gain factor to improve the visibility of P-waves, or may be unable to adequately adjust the gain to improve visibility.

This disclosure may involve adjusting gain factors for ECG displays, e.g., automatically. An example method of adjusting gain factors may include identifying P-waves within a cardiac signal stored by a medical device for a cardiac episode detected by the medical device and determining a gain factor for display of the cardiac signal based on the P-waves. In some examples, an example method may also determine that the cardiac episode is an atrial arrhythmia episode and automatically calculate the gain factor based on the P-waves based on the determination that the cardiac episode is an atrial arrhythmia episode. Gain factors for ECG displays may be adjusted through one or more of a method, processing circuitry in a medical device system, and instructions in a non-transitory computer-readable storage system.

In other examples, the techniques of this disclosure may be directed to a medical device system comprises processing circuitry that is configured to adjust gain factors of ECG displays. The processing circuitry of an example medical device system identify P-waves within a cardiac signal that is stored by a medical device for a cardiac episode detected by the medical device. The processing circuitry of an example system may be further configured to calculate a gain factor for display of the cardiac signal based on the identified P-waves.

In other examples, the techniques of this disclosure may be directed to a non-transitory computer-readable storage system comprises instructions that adjust gain factors of ECG displays. The instructions of an example non-transitory computer-readable storage system may, when executed by the processing circuitry of a medical device system, identify P-waves within a cardiac signal stored by a medical device for a cardiac episode detected by the medical device. The instructions may also, when executed by the processing circuitry of a medical device system, calculate a gain factor for display of the cardiac signal based on the identified P-waves.

The techniques of this disclosure may provide one or more advantages. For example, the techniques of this disclosure may simplify the observation of P-waves in the ECG display.

Figure 1:
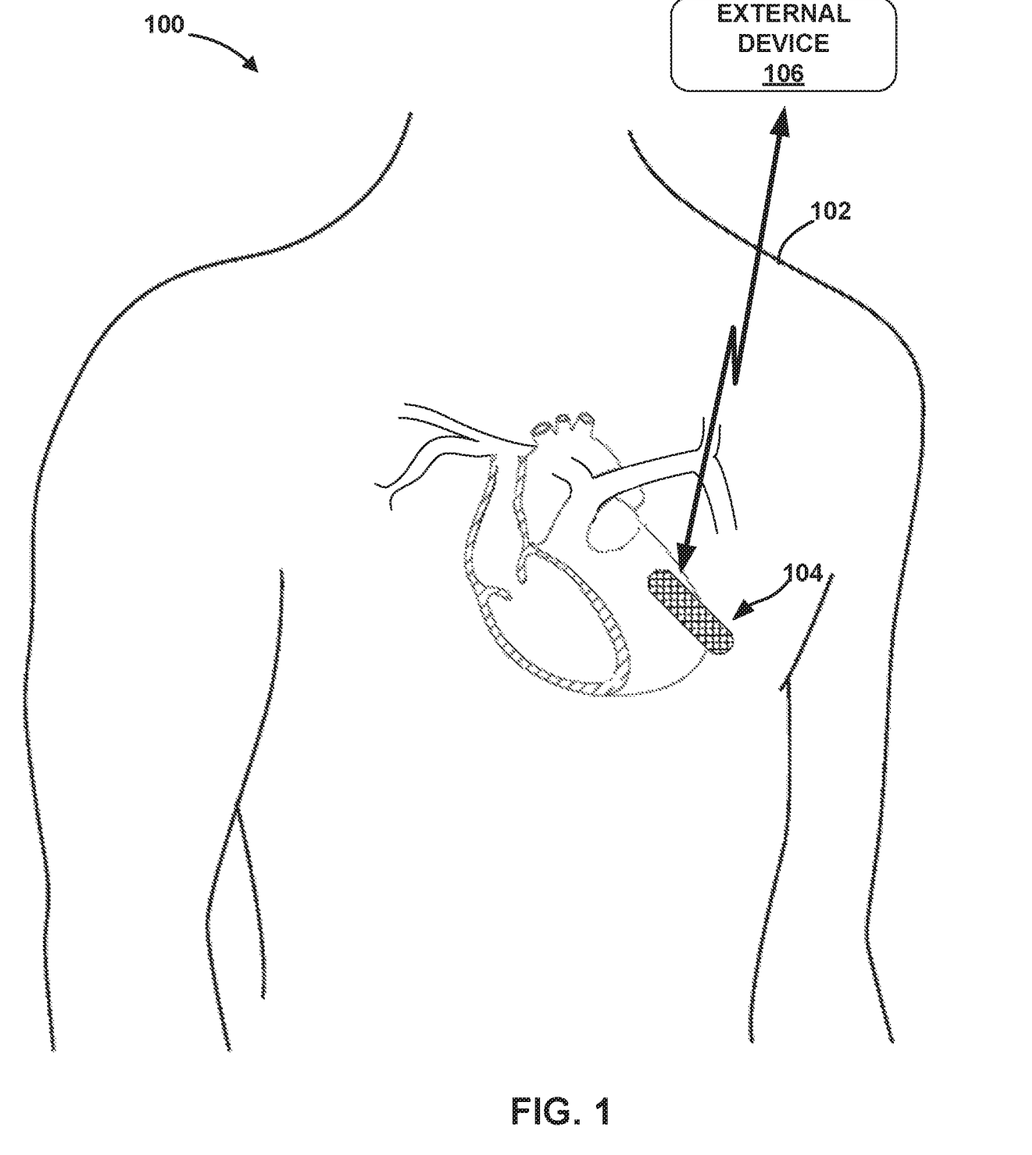
FIG. 1 illustrates the environment of an example medical device system in conjunction with a patient.

FIG. 1 illustrates the environment of an example medical device system 100 in conjunction with a patient 102, in accordance with an apparatus and method of certain examples described herein. The example techniques may be used with an IMD 104, which may be in wireless communication with at least one of external device 106 and other devices not pictured in FIG. 1. In some examples, IMD 104 is implanted outside of a thoracic cavity of patient 102 (e.g., subcutaneously in the pectoral location illustrated in FIG. 1). IMD 104 may be positioned near the sternum near or just below the level of the heart of patient 102, e.g., at least partially within the cardiac silhouette. IMD 104 includes a plurality of electrodes (not shown in FIG. 1) and is configured to sense a cardiac signal via the plurality of electrodes.

External device 106 may be a computing device with a display viewable by the user and an interface for providing input to external device 106 (i.e., a user input mechanism). In some examples, external device 106 may be a notebook computer, tablet computer, workstation, one or more servers, cellular phone, personal digital assistant, or another computing device that may run an application that enables the computing device to interact with IMD 104.

External device 106 is configured to communicate with IMD 104 and, optionally, another computing device (not illustrated in FIG. 1), via wireless communication. External device 106, for example, may communicate via near-field communication technologies (e.g., inductive coupling, NFC or other communication technologies operable at ranges less than 10-20 cm) and far-field communication technologies (e.g., radiofrequency (RF) telemetry according to the 802.11 or Bluetooth® specification sets, or other communication technologies operable at ranges greater than near-field communication technologies).

External device 106 may be used to configure operational parameters for IMD 104. External device 106 may be used to retrieve data from IMD 104. The retrieved data may include values of physiological parameters measured by IMD 104, indications of episodes of arrhythmia or other maladies detected by IMD 104, and physiological signals recorded by IMD 104. As will be discussed in greater detail below with respect to FIG. 5, one or more remote computing devices may interact with IMD 104 in a manner similar to external device 106, e.g., to program IMD 104 and/or retrieve data from IMD 104, via a network.

In some examples, external medical devices that may be used to non-invasively sense and monitor ECGs include wearable devices with electrodes configured to contact the skin of the patient, such as patched, watches, or necklaces. Such external devices may facilitate relatively longer-term monitoring of patients during normal daily activities and may periodically transmit collected data to a network service. In these examples, IMD 104 may not be required and components of IMD 104 (e.g., electrodes 218A and 218B, antenna 202, sensing circuitry 206, switching circuitry 212, sensors 214) may be components of an external medical device.

Figure 2:
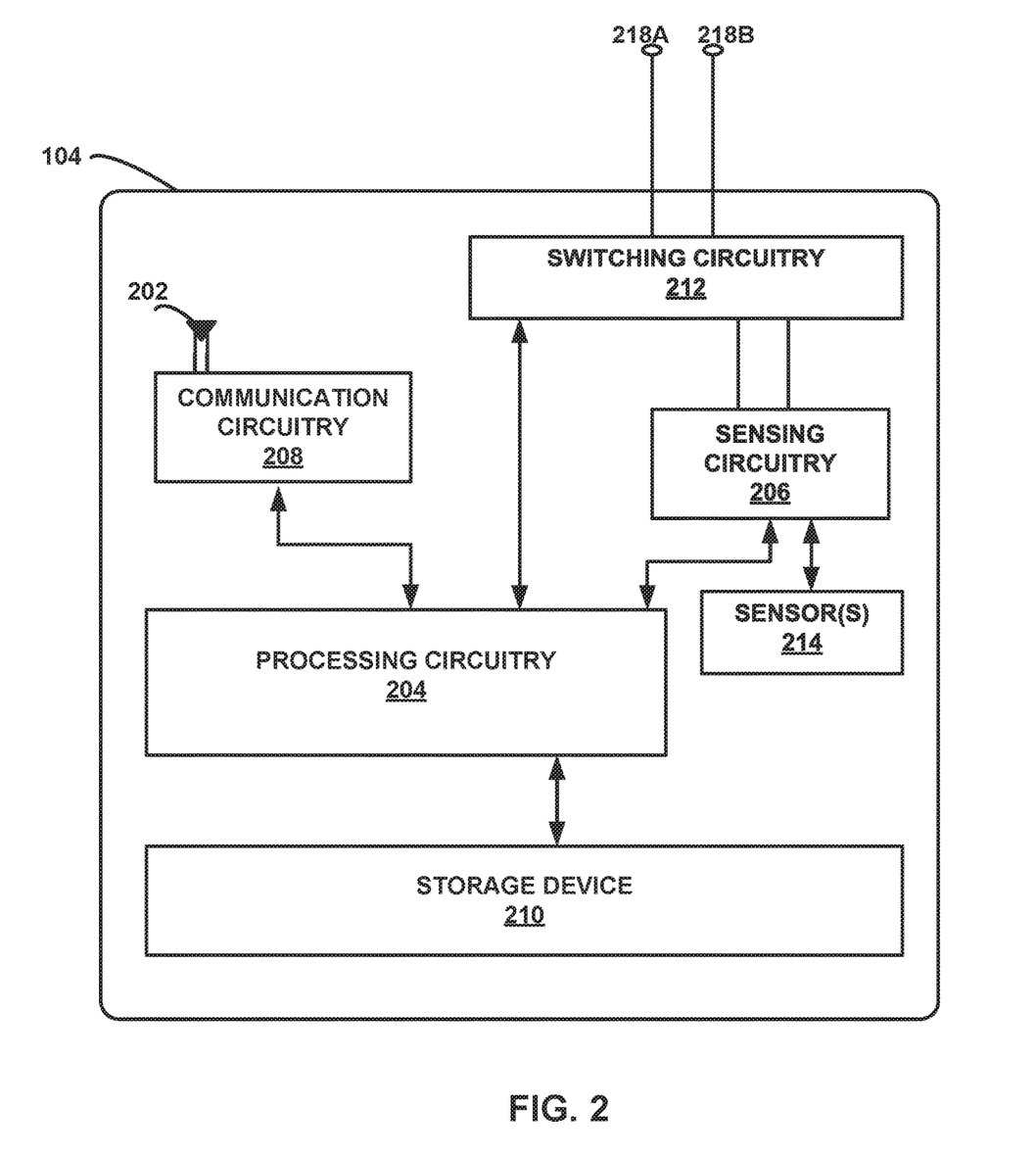
FIG. 2 is a functional block diagram illustrating an example configuration of the implanted medical device (IMD) of FIG. 1.

FIG. 2 is a functional block diagram illustrating an example configuration of IMD 104 of FIG. 1 in accordance with one or more techniques described herein. In the illustrated example, IMD 104 includes electrodes 218A and 218B (collectively "electrodes 218"), antenna 202, processing circuitry 204, sensing circuitry 206, communication circuitry 208, storage device 210, switching circuitry 212, and sensors 214. Although the illustrated example includes two electrodes 218, IMDs including or coupled to more than two electrodes 218 may implement the techniques of this disclosures in some examples. Electrodes 218 may be subcutaneous electrodes and IMD 104 may sense cardiac signals, e.g., ECGs, via subcutaneous electrodes.

Processing circuitry 204 may include fixed function circuitry and/or programmable processing circuitry. Processing circuitry 204 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 204 may include multiple components, such as any combination of one or more microprocessors, one or more controllers, one or more DSPs, one or more ASICs, or one or more FPGAs, as well as other discrete or integrated logic circuitry. The functions attributed to processing circuitry 204 herein may be embodied as software, firmware, hardware, or any combination thereof.

Sensing circuitry 206 may be selectively coupled to electrodes 218 via switching circuitry 212, e.g., to select the electrodes 218 and polarity, referred to as the sensing vector, used to sense cardiac signals indicating the electrical activity of the heart, as controlled by processing circuitry 204. Sensing circuitry 206 may sense signals from electrodes 218, e.g., to produce an ECG signal, in order to facilitate monitoring the electrical activity of the heart. Sensing circuitry 206 also may monitor signals from sensors 214, which may include one or more accelerometers, pressure sensors, and/or optical sensors, as examples. In some examples, sensing circuitry 206 may include one or more filters and amplifiers for filtering and amplifying signals received from electrodes 218 and/or sensors 214.

Sensing circuitry 206 and/or processing circuitry 204 may be configured to detect cardiac depolarizations (e.g., P-waves and/or R-waves) when the cardiac signal amplitude crosses a sensing threshold. In some examples, the sensing threshold is automatically adjustable over time using any of a variety of automatic sensing threshold adjustment techniques known in the art. For example, in response to detection of a cardiac depolarization, the sensing threshold for detecting a subsequent cardiac depolarization may decay from an initial value over a period of time. Sensing circuitry 206 and/or processing circuitry 204 may determine the initial value based on the amplitude of detected cardiac depolarization. The initial value and decay of the adjustable sensing threshold may be configured such that the sensing threshold is relatively higher soon after the detected cardiac depolarization when a subsequent depolarization is not expected, and decays to relatively lower values over time as the occurrence of a cardiac depolarization becomes more likely. For cardiac depolarization detection, sensing circuitry 206 may include a rectifier, filter, amplifier, comparator, and/or analog-to-digital converter, in some examples.

In some examples, sensing circuitry 206 may output an indication to processing circuitry 204 in response to sensing of a cardiac depolarization. In this manner, processing circuitry 204 may receive detected cardiac depolarization indicators corresponding to the occurrence of detected R-waves and P-waves in the respective chambers of heart. Processing circuitry 204 may use the indications of detected R-waves and P-waves for determining heart rate and detecting arrhythmia episodes, such as atrial and ventricular tachyarrhythmias.

Communication circuitry 208 may include any suitable hardware, firmware, software, or any combination thereof for communicating with another device, such as external device 106, another networked computing device, or another IMD or sensor. Under the control of processing circuitry 204, communication circuitry 208 may receive downlink telemetry from, as well as send uplink telemetry to external device 106 or another device with the aid of an internal or external antenna, e.g., antenna 202. In addition, processing circuitry 204 may communicate with a networked computing device via an external device (e.g., external device 106) and a computer network. Antenna 202 and communication circuitry 208 may be configured to transmit and/or receive signals via inductive coupling, electromagnetic coupling, Near Field Communication (NFC), Radio Frequency (RF) communications, Bluetooth, WiFi, or other proprietary or non-proprietary wireless communication schemes.

In some examples, storage device 210 may include computer-readable instructions that, when executed by processing circuitry 204, cause IMD 104 and processing circuitry 204 to perform various functions attributed to IMD 104 and processing circuitry 204 herein. Storage device 210 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Storage device 210 may store, as examples, programmed values for one or more operation parameters of IMD 104 and/or data collected by IMD 104 for transmission to another device using communication circuitry 208. Data stored by storage device 210 and transmitted by communication circuitry 208 to one or more other device may include episode data for suspected or potential arrhythmia episodes and/or data for detecting and/or identifying P-waves and R-waves in the cardiac signal.

In some examples, processing circuitry 204 circuitry may perform techniques, or portions of techniques, for determining a gain factor for display of a cardiac signal based on P-waves in the cardiac signals. Such operations may be performed on an analog version of the signal, a digital version of the signal, or in both the analog and digital domains.

For example, processing circuitry 204 may detect P-waves within a cardiac signal by averaging segments of the cardiac signal associated with R-waves that meet an RR interval selection criterion and detecting the presence of P-waves based on a derivative of the average of the segments of the cardiac signal. The RR interval selection criterion may be a determination of whether an RR interval between a currently sensed R-wave and a previously sensed R-wave is greater than a set interval threshold (e.g., an interval threshold of 780 ms). Processing circuitry 204 may average the amplitudes of a plurality of segments that meet the RR interval selection criterion (e.g., four cardiac signal segments that meet the RR interval selection criterion) to determine the average of the segment of the cardiac signal. Processing circuitry 204 may then rely on the first and/or second derivative of the average of the cardiac signal segments to detect the presence of P-waves. In some examples, processing circuitry 204 of IMD 104 may calculate the gain factor of the ECG signal based on the identified P-waves as described later with respect to FIG. 4.

Sensing circuitry 206 may provide one or more digitized ECG signals to processing circuitry 204 for analysis, e.g., for use in detecting P-waves in the ECG signals and/or for determining that the cardiac episode is an atrial arrhythmia episode. In some examples, processing circuitry 204 may store segments of the digitized ECG signal in storage device 210. The segments of digitized ECG signal may include segments that meet the RR interval selection criterion. Processing circuitry 204 of IMD 104, and/or processing circuitry of another device that retrieves data from IMD 104 (e.g., external device 106), may analyze the ECG segment to identify P-waves in the ECG signal and calculate the gain factor for the ECG signal based on the identified P-waves.

In other examples, processing circuitry 204 may analyze the ECG signals to determine a zoom factor for zooming in on a portion of the cardiac signal based on the gain factor.

Sensing circuitry 206 may also provide one of more digitized ECG signals to external device 104 for real-time or off-line analysis. Sensing circuitry 206 may also provide ECG data to external device 106 for real-time or off-line analysis. As an alternative, sensing circuitry 206 may also provide one or more digitized ECG signals to processing circuitry 206 for analysis.

Communication circuitry 208 may provide ECG data to external device 106 for real-time or off-line analysis, e.g., for use in identifying P-waves in the cardiac signal and calculating the gain factor for the cardiac signal based on the identified P-waves.

Figure 3:
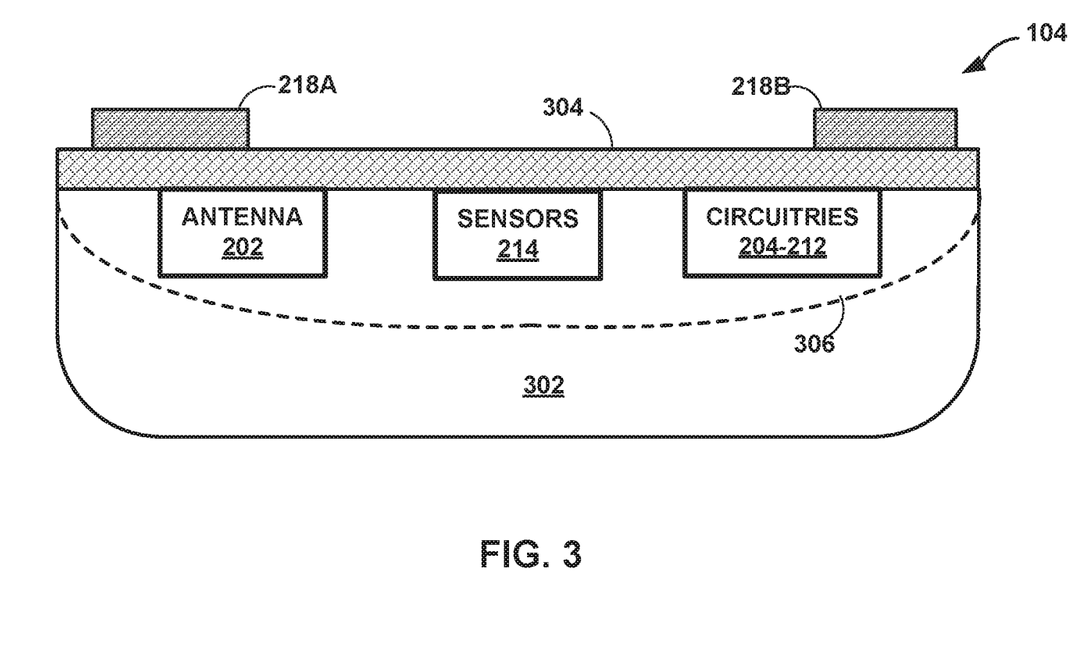
FIG. 3 is a conceptual side-view diagram illustrating an example configuration of the IMD of FIGS. 1 and 2.

FIG. 3 is a conceptual side-view diagram illustrating an example configuration of IMD 106 of FIGS. 1 and 2. In the example shown in FIG. 3, IMD 104 may include a leadless, subcutaneously-implantable monitoring device having a housing 302 and an insulative cover 304. Electrodes 218 may be formed or placed on an outer surface of insulative cover 304. Circuitries 204-212, described above with respect to FIG. 2, may be formed or placed on the outer surface in some examples. In some examples, insulative cover 304 may be positioned over an open housing 302 such that housing 302 and cover 304 enclose antenna 202 and circuitries 204-212 and protect the antenna and circuitries from fluids (e.g., body fluids).

One or more antenna 202 or circuitries 204-212 may be formed on the inner side of insulative cover 304, such as be using flip-chip technology. Insulative cover 304 may be flipped onto a housing 302. When flipped and placed onto housing 302, the components of IMD 104 formed on the inner side of insulative cover 304 may be positioned in a gap 306 through one or more vias (not shown) formed through insulative cover 304. Insulative cover 304 may be formed of sapphire (i.e., conundrum), glass, parylene, and/or any other suitable insulating material. Housing 302 may be formed from any of stainless steel, titanium, platinum, iridium, or alloys thereof. In addition, electrodes 218 may be coated with a material such as titanium nitride or fractal titanium nitride, although other suitable materials and coatings for such electrodes may be used.

Figure 4:
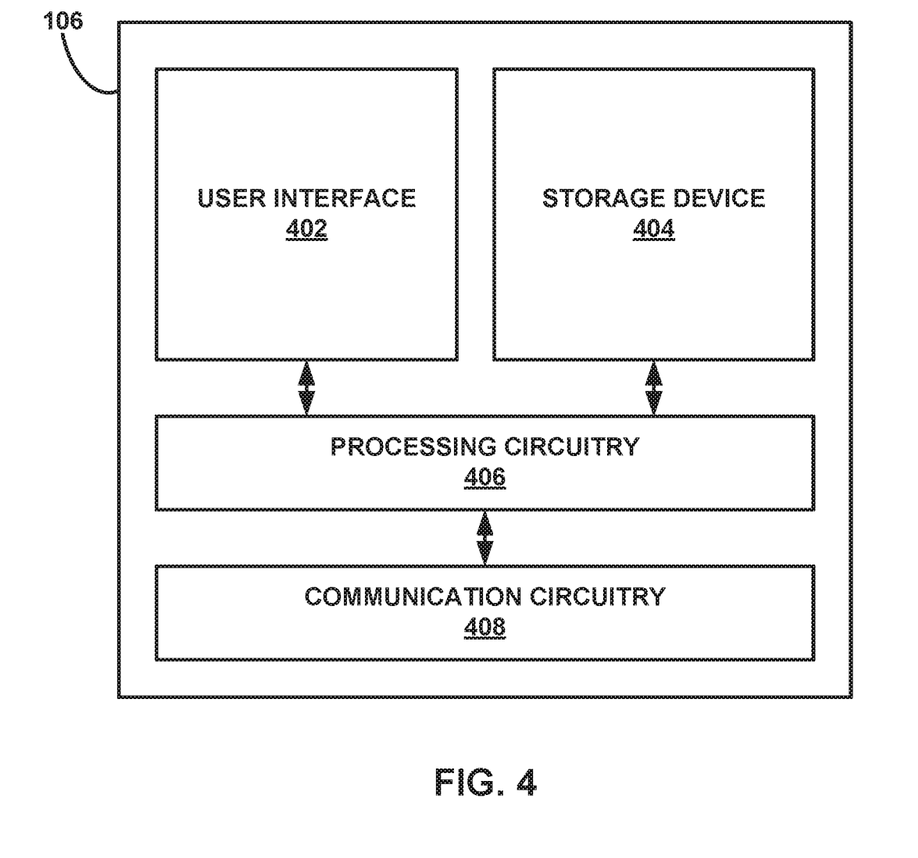
FIG. 4 is a functional block diagram illustrating an example configuration of the external device of FIG. 1.

FIG. 4 is a block diagram illustrating an example configuration of components of external device 106. In the example of FIG. 4, external device 106 includes user interface 402, storage device 404, processing circuitry 406, and communication circuitry 408.

Processing circuitry 406 may include one or more processors that are configured to implement functionality and/or process instructions for execution within external device 106. For example, processing circuitry 406 may be capable of processing instructions stored in storage device 84. Processing circuitry 406 may include, for example, microprocessors, DSPs, ASICs, FPGAs, or equivalent discrete or integrated logic circuitry, or a combination of any of the foregoing devices or circuitry. Accordingly, processing circuitry 406 may include any suitable structure, whether in hardware, software, firmware, or any combination thereof, to perform the functions ascribed herein to processing circuitry 406.

Communication circuitry 408 may include any suitable hardware, firmware, software or any combination thereof for communicating with another device, such as IMD 104. Under the control of processing circuitry 406, communication circuitry 408 may receive downlink telemetry from, as well as send uplink telemetry to IMD 104, or another device.

Communication circuitry may be configured to transmit or receive signals via inductive coupling, electromagnetic coupling, NFC, RF communication, Bluetooth, WiFi, or other proprietary or non-proprietary wireless communication schemes. Communication circuitry 408 may also be configured to communicate with device other than IMD 104 via any of a variety of forms of wired and/or wireless communication and/or network protocols.

Storage device 404 may be configured to store information within external device 106 during operation. Storage device 404 may include a computer-readable storage medium or computer-readable storage device. In some examples, storage device 404 includes one or more of a short-term memory or a long-term memory. Storage devices 404 may include, for example, RAM, DRAM, SRAM, magnetic discs, optical discs, flash memories, or forms of EPROM or EEPROM. In some examples, storage devices 404 is used to store data indicative of instructions for execution by processing circuitry 406. Storage device 404 may be used by software or applications running on external device 106 to temporarily store information during program execution.

Data exchanged between external device 106 and IMD 104 may include operational parameters. External device 106 may transmit data including computer readable instructions which, when implemented by IMD 104, may control IMD 104 to change one or more operational parameters and/or export collected data. For example, processing circuitry 406 may transmit an instruction to IMD 104 which requests IMD 104 to export collected data (e.g., segments of ECG signals and other information for episodes detected by IMD 104) to external device 106. In turn, external device 106 may receive the collected data from IMD 104 and store the collected data in storage device 404. Processing circuitry 406 may implement any of the techniques described herein to analyze ECGs received from IMD 104, e.g., to identify P-waves within the cardiac signal and/or to calculate a gain factor for display of the cardiac signal based on the identified P-waves.

Processing circuitry 406 may calculate the gain factor by determining an amplitude of each of the P-wave and determining an average, e.g., a mean, median, or other statistical representation, of the P-wave amplitudes. In some examples, processing circuitry 406 may determine the amplitude of each P-wave by determining the maximum amplitude of each P-wave, although other amplitude values for each P-wave, such as an amplitude at a particular point along or fraction of the length of the P-wave, are possible. In some examples, processing circuitry 406 may determine the average of the P-wave amplitudes by averaging the maximum amplitudes of a plurality of P-waves.

Processing circuitry 406 may then calculate, based on the average P-wave amplitudes, a gain factor based on the P-waves that translates the ECG signal to an ECG display, e.g., provided via a display of user interface 402. The gain factor may be greater than the standard gain factor (e.g., greater than 10 mm/mV). The gain factor based on P-waves may simplify user identification and use of P-waves on an ECG display. Processing circuitry 406 may also calculate a zoom factor for a cardiac signal display (e.g., ECG signal display) based on the gain factor that is based on the identified P-waves. The zoom factor may allow a user to zoom in on a portion of the cardiac signal with greater gain than the calculated gain factor.

A user, such as a clinician or patient 102, may interact with external device 106 through user interface 402. User interface 402 includes a display (not shown), such as a liquid crystal display (LCD) or a light emitting diode (LED) display or other type of screen, with which processing circuitry 406 may present information related to IMD 104, e.g., ECGs, gain factors based on the P-waves, zoom factors based on the P-waves, and/or ECG displays with the application of gain factors and zoom factors based on the P-waves. In addition, user interface 402 may include an input mechanism configured to receive input from the user. The input mechanisms may include, for example, any one or more buttons, a keypad (e.g., an alphanumeric keypad), a peripheral pointing device, a touch screen, or another input mechanism that allows the user to navigate through user interfaces presented by processing circuitry 406 of external device 106 and provide input. In other examples, user interface 402 also includes audio circuitry for providing audible notifications, instructions or other sounds to the user, receiving voice commands from the user, or both. In some examples processing circuitry 406 may, in response to user input, apply the zoom factor based on the gain factor based on the P-waves to the ECG display. In some examples, processing circuitry 406 provide the user options to switch the ECG display between a plurality of zoom factors.

Figure 5:
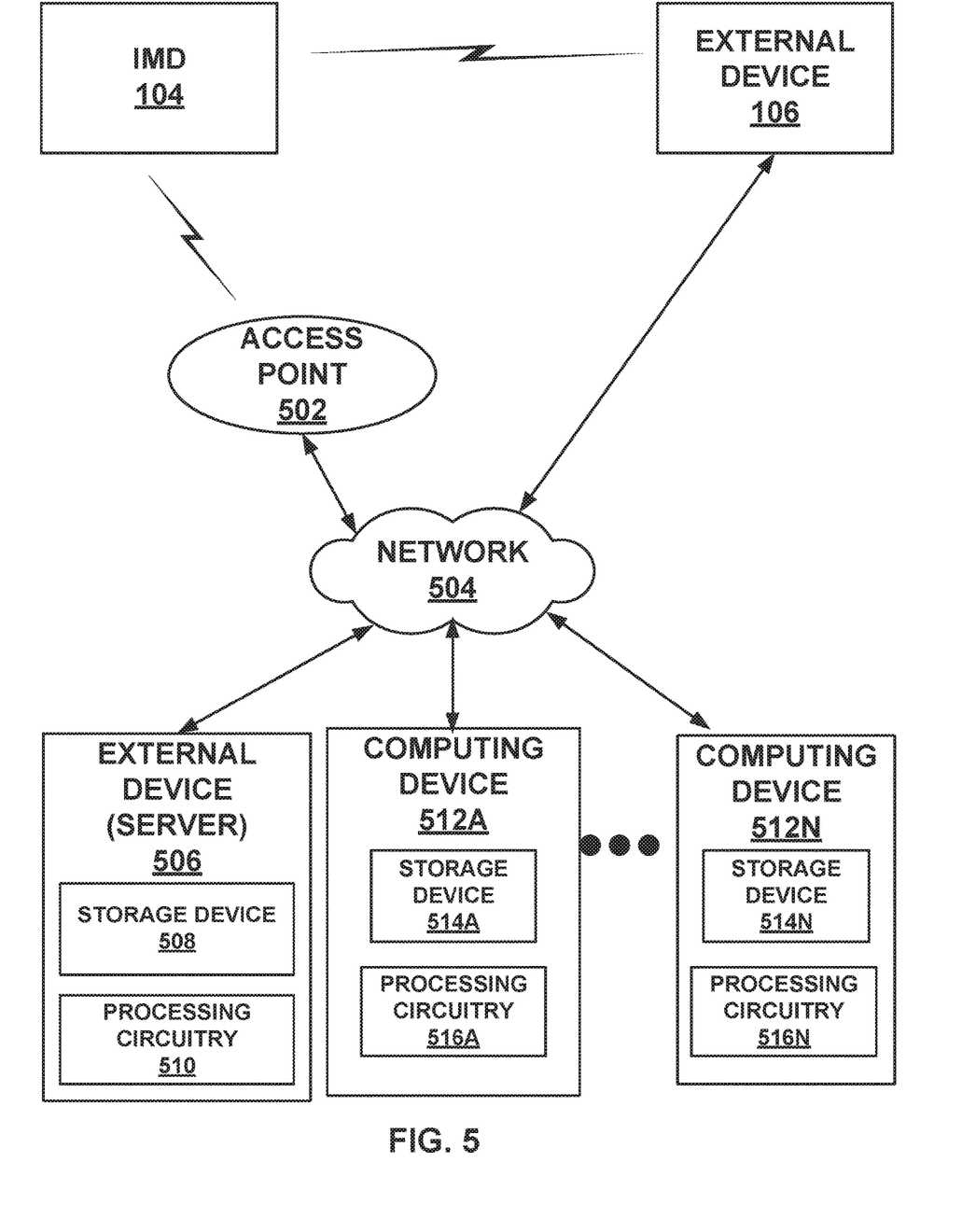
FIG. 5 is a block diagram illustrating an example system that includes an access point, a network, external computing devices, such as a server, and one or more other computing devices, which may be coupled to the IMD and external devices of FIGS. 1-4.

FIG. 5 is a block diagram illustrating an example system that includes an access point 502, a network 504, external computing devices, such as a server 506, and one or more other computing devices 512A-512N (collectively, "computing devices 512"), which may be coupled to the IMD 104 and external devices 106 of FIGS. 1-4. In this example, IMD 104 may user communication circuitry 208 to communicate with external device 106 via a first wireless connection and to communicate with an access point 502 via a second wireless connection. In the example of FIG. 5, access point 502, external device 106, server 506, and computing devices 512 are interconnected and may communicate with each other through network 504.

Access point 502 may include a device that connects to network 504 via any of a variety of connections, such as telephone dial-up, digital subscriber line (DSL), or cable modem connections. In other examples, access point 502 may be couple to network 504 through different forms of connections, including wired or wireless connections. In some examples, access point 502 may be a user device, such as a tablet or smartphone, that may be co-located with the patient. IMD 104 may be configured to transmit data, such as the identification of P-waves in ECG signals, to access point 502. Access point 502 may then communicate the retrieved data to server 506 via network 504.

In some cases, server 506 may be configured to provide a secure storage site for data that has been collected from IMD 104 and/or external device 106, e.g., episode data including associated ECGs or other cardiac signals. In some cases, server 506 may assemble data in web pages or other documents for viewing by trained professionals, such as clinicians, via computing devices 512. One or more aspects of the illustrated system of FIG. 5 may be implemented with general network technology and functionality.

In some examples, one or more of computing devices 512 may be a tablet or other smart device located with a clinician, by which the clinician may program, receive alerts from, and/or interrogate IMD 104. For example, the clinician may access data collected by IMD 104 through a computing device 512, such as when patient 102 is in between clinician visits, to check on a status of a medical condition. In some examples, the clinician may send, through computing devices 512, instructions to external devices 106 to change the gain factors and/or zoom factors of the ECG display outputted by user interface 402 of external devices 106.

In some examples, server 506 may include a storage device 508, e.g., to store data retrieved from IMD 104, and processing circuitry 510. Computing devices 512 may similarly include a storage device 514A-N (collectively, "storage devices" 514) and processing circuitry 516A-N (collectively, "processing circuitry" 516). Processing circuitry 510 may include one or more processors that are configured to implement functionality and/or process instructions for execution within server 506. For example, processing circuitry 510 may be capable of processing instructions stored in storage device 508. Processing circuitry 510 may include, for example, microprocessors, DSPs, ASICs, FPGAs, or equivalent discrete or integrated logic circuitry, or a combination of any of the foregoing devices or circuitry. Accordingly, processing circuitry 510 may include any suitable structure, whether in hardware, software, firmware, or any combination thereof, to perform the functions ascribed herein to processing circuitry 510. In some examples, processing circuitry 516 may include similar processors and have similar capabilities as processing circuitry 510 described above. Processing circuitry 510 of server 506 and/or the processing circuitry 516 may implement any of the techniques described herein to analyze ECG signals received from IMD 104, e.g., to determine calculate the gain factor for a display of cardiac signals based on identified P-waves.

Storage device 508 may include a computer-readable storage medium or computer-readable storage device. In some examples, storage device 508 includes one or more of a short-term memory or a long-term memory. Storage devices 508 may include, for example, RAM, DRAM, SRAM, magnetic discs, optical discs, flash memories, or forms of EPROM or EEPROM. In some examples, storage device 508 is used to store data indicative of instructions for execution by processing circuitry 510. In some examples, storage devices 514 may include the same devices and have similar functions as storage device 508.

Figure 6:
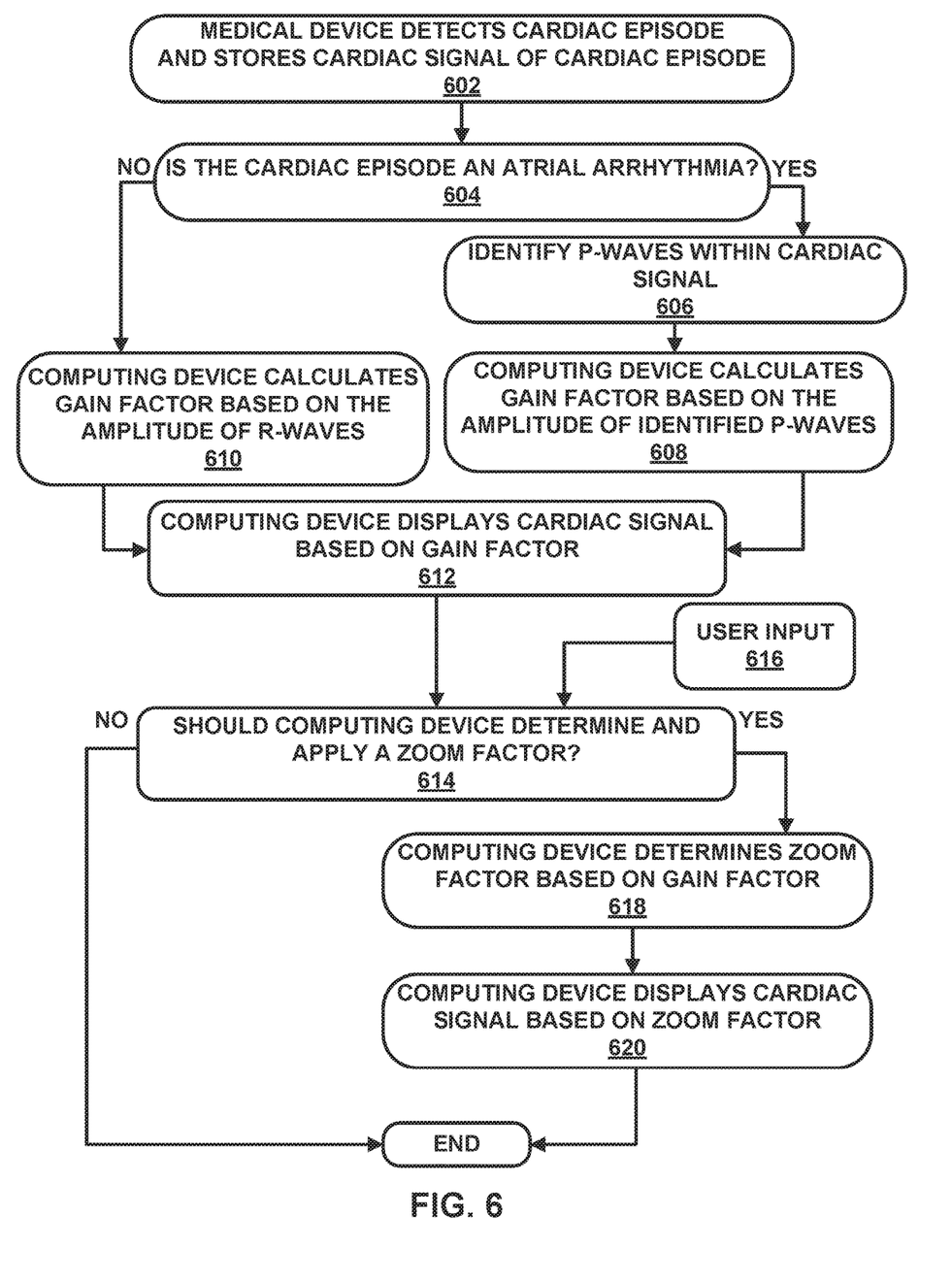
FIG. 6 is a flow diagram of an example method of adjusting a gain factor for ECG displays.

FIG. 6 is a flow diagram of an example method of adjusting a gain factor for ECG displays. For convenience, FIG. 6 is described with respect to FIGS. 1-5. While the method of FIG. 6 is described with respect to external device 106, IMD 104, server 506, and computing device 512 of FIGS. 1-5, in other examples, the method of FIG. 6 may be performed by other devices.

As depicted in FIG. 6, a medical device may detect a cardiac episode and store the cardiac signal or the cardiac episode (602). The medical device may be IMD 104 or external device 106 of FIGS. 1-4. The cardiac signal may be stored in storage device 210 of IMD 104, storage device 404 of external device 106, storage device 508 of server 506, and/or storage device 514 of one or more of computer device 512. The cardiac signal may be stored as an ECG signal and/or digitized ECG signal.

After a medical device detects a cardiac episode and stores the cardiac signal of the cardiac episode (602), processing circuitry 204 of IMD 104 and/or processing circuitry 406 of external device 106 may determine whether the detected cardiac episode is an atrial arrhythmia episode (604). In one example, processing circuitry 204 and/or processing circuitry 406 may determine that the detected cardiac episode is an atrial arrhythmia episode by determining that the heartbeat of patient 102 is irregular. In some examples, a medical device system may comprise processing circuitry that is configured to determine whether the detected cardiac episode is an atrial arrhythmia episode (604) in the manner described above. In other examples, a non-transitory computer-readable storage system may comprise instructions that, when executed by processing circuitry of a medical device system (e.g., processing circuitry 204 and/or processing circuitry 406), determines whether the detected cardiac episode is an atrial arrhythmia episode (606). While the example method of FIG. 6 includes the step of determining whether the detected cardiac episode is an atrial arrhythmia episode (604), other examples may proceed to identifying P-waves within the cardiac signal (606) without determining whether the detected cardiac episode is an atrial arrhythmia episode (604).

If an atrial arrhythmia episode is detected (YES branch of 604), processing circuitry 406 of external device 106, processing circuitry 510 of server 506, and/or processing circuitry 516 of computing device 512 may identify P-waves within the cardiac signal (606). Identifying P-waves within the cardiac signal (606) will be discussed in greater detail in FIG. 7. After P-waves are identified within the cardiac signal (606), processing circuitry 406, processing circuitry 510, and/or processing circuitry 516 may calculate a gain factor based on the amplitudes of the identified P-waves of the cardiac signal (608). Calculating a gain factor based on the amplitudes of the identified P-waves of the cardiac signal (608) will be discussed in greater detail in FIG. 8. In some examples, the medical device system may comprise processing circuitry (e.g., processing circuitry 406, processing circuitry 510, processing circuitry 516) configured to identify P-waves within the cardiac signal (606) and calculate a gain factor based on the amplitudes of the identified P-waves of the cardiac signal (608). In other examples, a non-transitory computer-readable storage system may comprise instructions that, when executed by processing circuitry of a medical device system (e.g., processing circuitry 406, processing circuitry 510, and/or processing circuitry 516), may identify P-waves of the cardiac signal (606) and calculate a gain factor based on the amplitudes of the identified P-waves of the cardiac signal (608).

If an atrial arrhythmia episode is not detected (NO branch of 604), processing circuitry 406, processing circuitry 510, and/or processing circuitry 516 may calculate the gain factor based on the amplitude of R-waves of the cardiac signal (610). Processing circuitry 406, processing circuitry 510, and/or processing circuitry 516 may calculate the gain factor based on the amplitude of R-waves of the cardiac signal (610) by determining an appropriate gain factor to display the cardiac signal onto an ECG display in external device 106 and/or computing device 512. Calculating the gain factor based on the amplitude of R-waves of the cardiac signal (610) may be done by any known methods within the art. For example, processing circuitry 406 may determine, based on the maximum amplitudes of the R-waves of the cardiac signal, that a standard gain factor of 10 mm/mV is sufficient to display the ECG signal on a computing device 512 (e.g., laptop). In some examples, processing circuitry 406, processing circuitry 510, and/or processing circuitry 516 may calculate the gain factor based on the amplitude of R-waves of the cardiac signal (610). In some examples, a medical device system may comprise processing circuitry (e.g., processing circuitry 406, processing circuitry 510, and/or processing circuitry 516) configured to calculate a gain factor based on the amplitude of R-waves of the cardiac signal (610). In other examples, a non-transitory computer-readable storage system may comprise instructions that, when executed by processing circuitry of a medical device system (e.g., processing circuitry 406, processing circuitry 510, and/or processing circuitry 516), may calculate a gain factor based on the amplitude of R-waves of the cardiac signal (610).

After the gain factor is calculated, either based on the amplitudes of the R-waves of the cardiac signal (610) or based on the amplitudes of the identified P-waves of the cardiac signal (608), processing circuitry 406 of external device 106, processing circuitry 510 of server 506, and/or processing circuitry 516 of computing device 512 may then display the cardiac signal based on the gain factor (612). In some examples, processing circuitry 406, processing circuitry 510, and/or processing circuitry 516 may display the cardiac signal in an ECG display using the calculated gain factor. Processing circuitry 406, processing circuitry 510, and/or processing circuitry 516 may display the cardiac signal on one or more computing devices 512 and/or displays of external device 106. In some examples, the R-waves corresponding to the displayed P-waves may be fully displayed on display of external device 106 and computing device 512. In other examples, the R-waves corresponding to the displayed P-waves may only be partially displayed. In some examples, a medical device system may comprise processing circuitry (e.g., processing circuitry 406, processing circuitry 510, and/or processing circuitry 516) configured to display the cardiac signal based on the gain factor (612). In other examples, a non-transitory computer-readable storage system may comprise instructions that, when executed by processing circuitry of a medical device system (e.g., processing circuitry 406, processing circuitry 510, and/or processing circuitry 516), may display the cardiac signal based on the gain factor (612).

After the cardiac signal based on the gain factor is displayed (612), processing circuitry 406, processing circuitry 510, and/or processing circuitry 516 may then determine whether to determine and apply a zoom factor (614). In the example of FIG. 6, processing circuitry 406, processing circuitry 510, and/or processing circuitry 516 may rely on user input 616 to determine whether to determine and apply a zoom factor (614). For example, a user may input instructions to computing device 512 to determine and apply a zoom factor. If processing circuitry 406, processing circuitry 510, and/or processing circuitry 516 determines not to determine and apply a zoom factor (NO branch of 614), the example method of FIG. 6 ends. If processing circuitry 406, processing circuitry 510, and/or processing circuitry 516 determines to determine and apply a zoom factor (YES branch of 614), processing circuitry 406, processing circuitry 510, and/or processing circuitry 516 then determines a zoom factor based on the gain factor (618). Processing circuitry 406, processing circuitry 510, and/or processing circuitry 516 may determine the zoom factor as the ratio of the gain factor based on the identified P-waves of the cardiac signal to a standard gain factor. For example, if the calculated gain factor based on the identified P-waves of the cardiac signal is 20 mm/mV and the standard gain factor of computing device 512 or display of external device 106 is 10 mm/mV, then processing circuitry 406, processing circuitry 510, and/or processing circuitry 516 may determine the zoom factor as 1.5. In some examples, computing device 512 and/or display of external device 106 may display zoom factor as e.g., "150%" or "1.5×". In some examples, a medical device system may comprise processing circuitry (e.g., processing circuitry 406, processing circuitry 510, and/or processing circuitry 516) configured to determine whether to determine and apply a zoom factor (614), which may be based on user input (616), and determine a zoom factor based on the gain factor (618). In other examples, a non-transitory computer-readable storage system may comprise instructions that, when executed by processing circuitry of a medical device system (e.g., processing circuitry 406, processing circuitry 510, and/or processing circuitry 516), determines whether to determine and apply a zoom factor (614), which may be based on user input (616), and determine a zoom factor based on the gain factor (618).

After processing circuitry 406, processing circuitry 510, and/or processing circuitry 516 determines the zoom factor based on the gain factor (618), processing circuitry 406, processing circuitry 510, and/or processing circuitry 516 may then display the cardiac signal based on the zoom factor (620). Computing device 512 and/or display of external device 106 may display the cardiac signal based on the zoom factor by increasing the magnitude of the cardiac signals by the zoom factor and displaying the modified zoom factor on computing device 512 and/or display of external device 106. After computing device 512 and/or display of external device 106 displays the cardiac signal based on the zoom factor (620), the example method of FIG. 6 ends. In some examples, a medical device system may comprise processing circuitry (e.g., processing circuitry 406, processing circuitry 510, and/or processing circuitry 516) configured to display the cardiac signal based on the zoom factor (620). In other examples, a non-transitory computer-readable storage system may comprise instructions that, when executed by processing circuitry of a medical device system (e.g., processing circuitry 406, processing circuitry 510, and/or processing circuitry 516), displays the cardiac signal based on the zoom factor (620).

Figure 7:
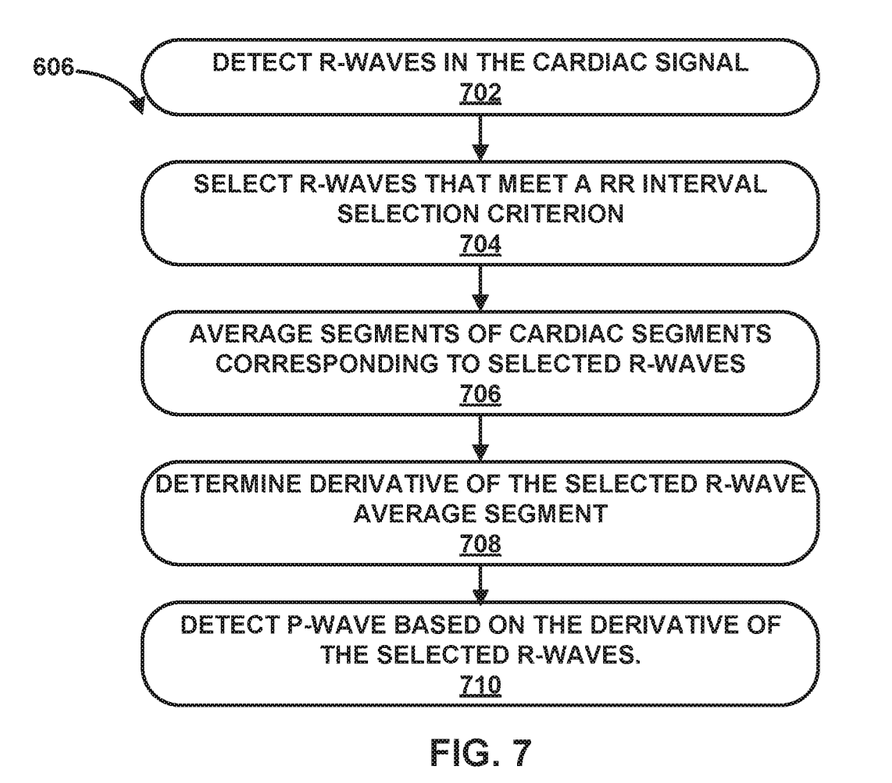
FIG. 7 is a flow diagram of an example method of identifying P-waves in a cardiac signal of the method of FIG. 6.

FIG. 7 is a flow diagram of an example method of determining the presence of P-waves in a cardiac signal (606) of the method of FIG. 6. For convenience, FIG. 7 is described with respect to FIGS. 1-5. While the method of FIG. 7 is described with respect to external device 106, IMD 104, server 506, and computing device 512 of FIGS. 1-5, in other examples, the method of FIG. 7 may be performed by other devices.

As depicted in FIG. 7, IMD 104, external device 106, server 506 and/or computing device 512 may detect R-waves in the cardiac signal stored in a medical device (702). Specifically, processing circuitry 204 of IMD 104, processing circuitry 406 of external device 106, processing circuitry 510 of server 506, and/or processing circuitry 516 of computing device 512 may detect R-waves in the cardiac signal (702). The medical device may be IMD 104 and/or external device 106. R-waves may be detected using any of a plurality of techniques known in the art. For example, electrodes attached to IMD 104 may be connected to the ventricles of the heart of the patient 102 that senses R-waves in the ventricles. In other examples, external device 106 may include monitors having ECG electrodes coupled to the skin of the patient 102 to detect R-waves (e.g., Holter monitors). In some examples, segments of the cardiac signal corresponding to the detected R-waves may be stored in storage device 210 of IMD 104, storage device 404 of external device 106, storage device 508 of server 506, and/or storage device 514 of computing device 512.

After detecting R-waves in the cardiac signal, processing circuitry 204 of IMD 104, processing circuitry 406 of external device 106, processing circuitry 510 of server 506, and/or processing circuitry 516 of computing device 512 may select R-waves that meet a RR interval selection criterion (704). The R-waves may be selected from a plurality of R-waves detected by processing circuitry 204, processing circuitry 406, processing circuitry 510, and/or processing circuitry 516. In some examples, the RR interval selection criterion may be a determination of whether an RR interval between a currently sensed R-wave and a previously sensed R-wave is greater than a set interval threshold (e.g., an interval threshold of 780 ms). For example, if the RR interval between a currently sensed R-wave and a previously sensed R-wave is 800 ms and the set interval threshold is 780 ms, then processing circuitry 204, processing circuitry 406, processing circuitry 510, and/or processing circuitry 516 may determine that the currently sensed R-wave meets the RR interval selection criterion and select the currently sensed R-wave. In some examples, segments of the cardiac signal corresponding to R-waves that meet the RR interval selection criterion may be stored in storage device 210, storage device 404, storage device 508, and/or storage device 514.

Processing circuitry 204 of IMD 104, processing circuitry 406 of external device 106, processing circuitry 510 of server 506, and/or processing circuitry 516 of computing device 512 may then average segments of the cardiac signal corresponding to the selected R-waves (706). The average segment may represent the average amplitude of the segments of the selected R-waves over a period of time. In some examples, processing circuitry 204, processing circuitry 406, processing circuitry 406, processing circuitry 510, and/or processing circuitry 516 may average segments of the cardiac signal corresponding to a plurality of R-waves encompassing a portion of the selected R-waves. For example, processing circuitry 204, processing circuitry 406, processing circuitry 510, and/or processing circuitry 516 may average segments of the cardiac signal corresponding to four selected R-waves and determine an average segment of the cardiac signal corresponding to the selected R-waves. In some examples, processing circuitry 204, processing circuitry 406, processing circuitry 510, and/or processing circuitry 516 may average segments of the cardiac signal corresponding to every selected R-wave. The average segment may be stored in storage device 210, storage device 404, storage device 508, and/or storage device 514.

Processing circuitry 204 of IMD 104, processing circuitry 406 of external device 106, processing circuitry 510 of server 506, and/or processing circuitry 516 of computing device 512 may then determine one or more derivatives of the average segments of the selected R-waves (708). The one or more derivatives may consist of one or more first and/or second derivatives of the average segment of the selected R-waves. In some examples, the one or more derivatives of the average segment may be stored in storage device 210, storage device 404, storage device 508, and/or storage device 514.

After determining one or more derivatives of the average segments of the selected R-waves (708), processing circuitry 204 of IMD 104, processing circuitry 406 of external device 106, processing circuitry 510 of server 506, and/or processing circuitry 516 of computing device 512 may then detect P-waves based on the one or more derivatives of the average segments of the select R-waves (710).). In some examples, processing circuitry 204, processing circuitry 406, processing circuitry 510, and/or processing circuitry 516 may determine a sensing window for the cardiac signal and determine signal characteristics of the sensed cardiac signal within the sensing window. processing circuitry 204, processing circuitry 406, processing circuitry 510, and/or processing circuitry 516 may then determine whether a signal-to-noise ratio corresponding to the cardiac signal within the sensing window is satisfied based on the amplitudes of the second derivative of the average segments of the selected R-waves. In some examples, the signal-to-noise ratio is satisfied when the maximum amplitude of the second derivative signal is greater than the maximum amplitude of the first derivative signal by a predetermined amplitude variation threshold (e.g., the maximum amplitude of the second derivative signal is greater than four times the maximum amplitude of the first derivative signal). In other examples, the signal-to-noise ratio is satisfied when the minimum amplitude of the second derivative signal is less than the minimum amplitude of the first derivative signal by a predetermined amplitude variation threshold (e.g., the minimum amplitude of the first derivative signal is greater than four times the minimum amplitude of the second derivative signal). Based on a determination that the signal-to-noise ratio is satisfied, processing circuitry 204, processing circuitry 406, processing circuitry 510, and/or processing circuitry 516 may then determine the presence of and record P-waves in the cardiac signal. P-waves and/or segments of the cardiac signal corresponding to P-waves may be recorded in in storage device 210, storage device 404, storage device 508, and/or storage device 514.

Figure 8:
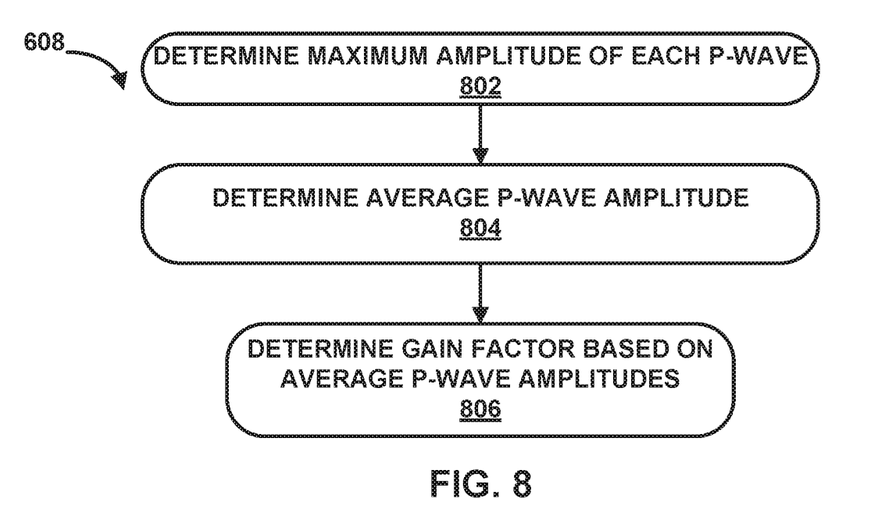
FIG. 8 is a flow diagram of an example method of calculating the gain factor of the method of FIG. 6.

FIG. 8 is a flow diagram of an example method of computing device 512 calculating the gain factor based on the amplitudes of the identified P-waves (608) of the method of FIG. 6. For convenience, FIG. 8 is described with respect to FIGS. 1-7. While the method of FIG. 8 is described with respect to external device 106, server 506, and computing device 512 of FIGS. 1-5, in other examples, the method of FIG. 8 may be performed by other devices.

Processing circuitry 406 of external device 106, processing circuitry 510 of server 506, and/or processing circuitry 516 of computing device 512 may first determine the maximum amplitude of each detected P-wave (802). Processing circuitry 406, processing circuitry 510, and/or processing circuitry 516 may determine the maximum amplitude of each detected P-wave (802) by accessing the detected P-waves that may be stored in storage device 210, storage device 404, storage device 508, and/or storage device 514. The determined maximum amplitudes of the detected P-waves may then be stored in storage device 404, storage device 508, and/or storage device 514.

Based on the determined maximum amplitudes of the detected P-waves, processing circuitry 406, processing circuitry 510, and/or processing circuitry 516 may then determine an average P-wave amplitude (804). In some examples, processing circuitry 406, processing circuitry 510, and/or processing circuitry 516 may determine the average P-wave amplitude based on the maximum amplitudes a plurality of detected P-waves encompassing a portion of the plurality of P-waves detected by IMD 104, external device 106, server 506, and/or computing device 512. For example, processing circuitry 406, processing circuitry 510, and/or processing circuitry 516 may determine the average P-wave amplitude based on the maximum amplitude of four detected P-waves. In other examples, processing circuitry 406, processing circuitry 510, and/or processing circuitry 516 may determine the average P-wave amplitude based on the maximum amplitudes of all detected P-waves. The average P-wave amplitude may be stored in storage device 404, storage device 508, and/or storage device 514.

Processing circuitry 406, processing circuitry 510, and/or processing circuitry 516 may then determine a gain factor based on the average P-wave amplitudes (806). Known methods to determine a gain factor based on R-wave amplitudes may be used to determine the gain factor based on the average P-wave amplitudes. In one example, processing circuitry 406, processing circuitry 510, and/or processing circuitry 516 may, based on display requirements of external device 106, server 506, and/or computing device 512, determine a gain factor based on the average P-wave amplitudes that appropriately scales the detected P-waves of the cardiac signal to the display requirements. For example, if the maximum amplitudes of P-waves on the display of the external device 106 need to be at least 1 cm in height and the P-wave average amplitude is 0.5 mV, then processing circuitry 406, processing circuitry 510, and/or processing circuitry 516 may determine a gain factor of 20 mm/mV. The determined gain factor may be stored in storage device 404, storage device 508, and/or storage device 514. The gain factor may be used by external device 106, server 506, and/or computing device 512 for the display of subsequent and/or future cardiac episodes.

Figure 9A:
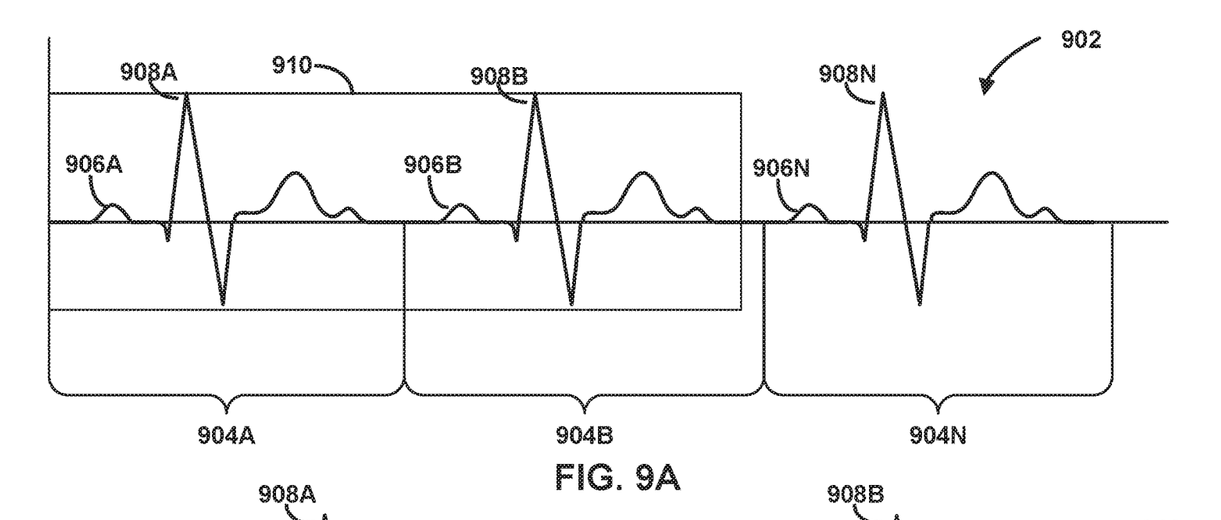
FIG. 9A is an example ECG plot displayed by an example computing device for an episode collected by the example medical device system of FIG. 1-4.

FIG. 9A is an example ECG plot displayed by an example computing device for an episode collected by the example medical device system of FIG. 1-5. ECG display using a standard gain factor 902 displays the ECG signal of an example cardiac signal of an example cardiac episode. The ECG signal may comprise a plurality of ECGs of individual cardiac cycles 904A-N (herein referred to as "cardiac cycle ECG" 904). Each cardiac cycle ECG 904 comprises the distinct components of an ECG signal described earlier, including P-waves 906A-N (herein referred to as "P-wave" 906), Q-waves, R-waves 908A-N (herein referred to as "R-wave" 908), S-waves, and T-waves. ECG display using a standard gain factor 902 displays the ECG signal based on a standard gain factor (e.g., 10 mm/mV) or a gain factor based on R-waves of the cardiac signal. ECG display using a gain factor based on the identified P-waves 910 may be seen alongside ECG display using a standard gain factor 902. The example ECG plot of FIG. 9A may be displayed on the display of external device 106, computing device 512, or any other device disclosed herein.

Figure 9B:
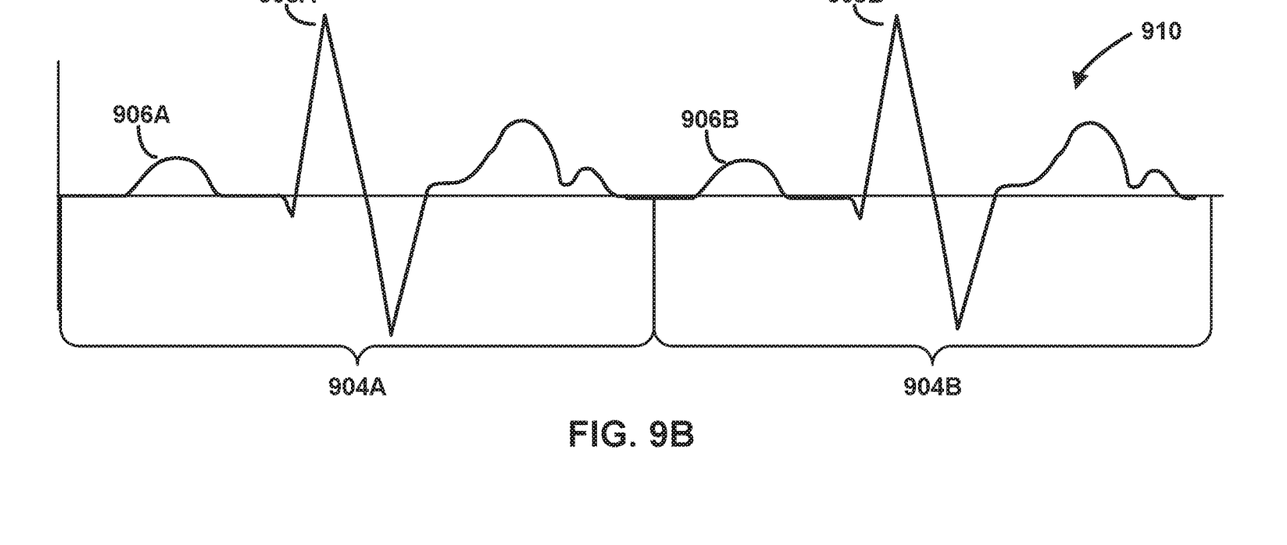
FIG. 9B is an example ECG plot of FIG. 9A, enhanced by an example zoom factor.

FIG. 9B is an example ECG display of FIG. 9A, using an example gain factor based on the identified P-waves. The example ECG display of FIG. 9B may be produced using the techniques disclosed above. In ECG display using a gain factor based on the identified P-waves 910, the P-waves 906 and R-waves 908 may be more visible to users. In some cases, the entire R-waves 908 may be visible on ECG display using a gain factor based on the identified P-waves 910. In other cases, only portions of the R-waves 908 may be visible. The example ECG plot of FIG. 9B may be displayed on the display of external device 106, computing device 512, or any other device disclosed herein. An example ECG display of FIG. 9B may be generated in real-time or in post-episode analysis.

Although described herein primarily in the context of examples in which a gain factor for displaying a cardiac signal an episode is either calculated based on P-waves, or is standard or based on R-waves, in some examples multiple gain factors may be used for a given episode, and respectively applied for displaying different portions of the episode. In some examples, a gain factor calculated based on one or more P-waves of an episode may be used to display one or more portions or windows of the episode that include P-waves. Other portions of the episode, e.g., windows including R-waves, may be displayed using a standard gain factor or a gain factor calculated based on R-wave amplitudes. In this manner, processing circuitry may facilitate the display of different windows of the cardiac signal using a gain factor that allows ready viewing of the waves therein.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module, unit, or circuit for purposes of clarity, it should be understood that the techniques of this disclosure may be performed by a combination of units, modules, or circuitry associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Various examples have been described. These and other examples are within the scope of the following claims.

What is claimed is:

1. A method for controlling operation of processing circuitry of a system, the method comprising:
    identifying, by the processing circuitry, P-waves within a cardiac signal stored by an implantable medical device for a cardiac episode detected by the implantable medical device;
    determining, by the processing circuitry, a gain factor for the cardiac signal based on the identified P-waves;
    applying, by the processing circuitry, the determined gain factor to convert the cardiac signal to a displayable cardiac signal; and
    causing, by the processing circuitry, the displayable cardiac signal to be displayed on a display.

2. The method of claim 1, further comprising determining, by the processing circuitry, that the episode is an atrial arrhythmia episode detected by the implantable medical device, wherein determining the gain factor comprises automatically determining the gain factor based on the identified P-waves based on the determination that the episode is an atrial arrhythmia episode.

3. The method of claim 1, wherein identifying the P-waves comprises detecting each of the P-waves by at least:
    averaging segments of the cardiac signal associated with R-waves that meet an RR interval selection criterion; and
    detecting the respective P-wave based on a derivative of the average of the segments.

4. The method of claim 1, wherein determining the gain factor comprises:
    determining an amplitude of each of the P-waves, and
    determining an average of the P-wave amplitudes.

5. The method of claim 4, wherein the amplitude of each P-wave is determined based on a maximum value of the cardiac signal for the respective P-wave.

6. The method of claim 1, further comprising determining, by the processing circuitry, a zoom factor for zooming in on a portion of the cardiac signal based on the gain factor.

7. The method of claim 6, further comprising applying, by the processing circuitry, the zoom factor in response to user input.

8. The method of claim 1, wherein determining the gain factor comprises:
   determining a first gain factor based on the identified P-waves of a first portion of the cardiac signal that includes at least one of the P-waves; and
   determining a second gain factor, different than the first gain factor, of a second portion of the cardiac signal that does not include any of the identified P-waves,
   wherein applying the determined gain factor comprises:
      applying the determined first gain factor to convert the first portion of the cardiac signal to a first displayable cardiac signal; and
      applying the determined second gain factor to convert the second portion of the cardiac signal to a second displayable cardiac signal, and
   wherein causing the displayable cardiac signal to be displayed comprises:
      causing one or more of the first displayable cardiac signal or the second displayable cardiac signal to be displayed on the display.

9. The method of claim 1, wherein the cardiac signal comprises a cardiac signal sensed via subcutaneous electrodes.

10. A medical device system comprising processing circuitry configured to:
    identify P-waves within a cardiac signal stored by an implantable medical device for a cardiac episode detected by the implantable medical device;
    determine a gain factor for the cardiac signal based on the identified P-waves;
    apply the determined gain factor to convert the cardiac signal to a displayable cardiac signal; and
    cause the displayable cardiac signal to be displayed on a display.

11. The system of claim 10, wherein the processing circuitry is further configured to determine that the episode is an atrial arrhythmia episode detected by the implantable medical device, wherein the processing circuitry is configured to determine the gain factor based on the identified P-waves based on the determination that the episode is an atrial arrhythmia episode.

12. The system of claim 10, wherein the processing circuitry is configured to identify P-waves by at least:
    averaging segments of the cardiac signal associated with R-waves that meet a RR interval selection criterion; and
    detecting the P-waves based on a derivative of the average of the segments.

13. The system of claim 10, wherein the processing circuitry comprises processing circuitry of a computing system configured to wirelessly communicate with the implantable medical device.

14. The system of claim 10, wherein, to determine the gain factor, the processing circuitry is configured to:
    determine an amplitude for each of the P-waves; and
    determine an average of the P-wave amplitudes.

15. The system of claim 14, wherein the processing circuitry is configured to determine the amplitude of each P-wave based on a maximum value of the cardiac signal for the respective P-wave.

16. The system of claim 10, wherein the processing circuitry is further configured to determine a zoom factor for zooming in on a portion of the cardiac signal based on the gain factor.

17. The system of claim 16, wherein the processing circuitry is configured to apply the zoom factor in response to user input.

18. The system of claim 10, wherein the gain factor comprises a first gain factor, and the processing circuitry is configured to:
    determine the first gain factor based on the identified P-waves of a first portion of the cardiac signal that includes at least one of the P-waves;
    determine a second gain factor, different than the first gain factor, of a second portion of the cardiac signal that does not include any of the identified P-waves;
    apply the determined first gain factor to convert the first portion of the cardiac signal to a first displayable cardiac signal;
    apply the determined second gain factor to convert the second portion of the cardiac signal to a second displayable cardiac signal; and
    cause one or more of the first displayable cardiac signal or the second displayable cardiac signal to be displayed on the display.

19. The system of claim 10, wherein the processing circuitry is configured to:
    determine a type of the episode; and
    based on the type of the episode, determine whether to identify the P-waves and determine the gain factor for the cardiac signal based on the identified P-waves.

* * * * *